(12) United States Patent
Nagayoshi

(10) Patent No.: US 6,657,722 B1
(45) Date of Patent: Dec. 2, 2003

(54) SIDE MULTIPLE-LAMP TYPE ON-LINE INSIDE QUALITY INSPECTING DEVICE

(75) Inventor: Atsuhiro Nagayoshi, Shizuoka (JP)

(73) Assignee: Kabushikaisha Kajitsuhihakaihinshitsukenkyujo, Shizuoka (JP)

( * ) Notice: Subject to any disclaimer, the term of this patent is extended or adjusted under 35 U.S.C. 154(b) by 146 days.

(21) Appl. No.: 10/019,107

(22) PCT Filed: Jun. 20, 2000

(86) PCT No.: PCT/JP00/04005

§ 371 (c)(1),
(2), (4) Date: Dec. 20, 2001

(87) PCT Pub. No.: WO00/79247

PCT Pub. Date: Dec. 28, 2000

(30) Foreign Application Priority Data

Jun. 21, 1999  (JP) ............................................. 11-173916

(51) Int. Cl.[7] .................................................. G01J 3/28
(52) U.S. Cl. ........................ 356/326; 356/330; 356/310; 250/223 R; 250/910; 209/577
(58) Field of Search ................................ 356/326, 330, 356/310; 250/226, 223 R, 910; 209/577, 580–581

(56) References Cited

U.S. PATENT DOCUMENTS

| | | | | |
|---|---|---|---|---|
| 3,735,143 A | * | 5/1973 | Langford | ..................... 250/226 |
| 4,150,287 A | | 4/1979 | Perkins | |
| 5,345,081 A | * | 9/1994 | Rogers | .................... 250/223 R |
| 5,401,954 A | | 3/1995 | Richert | |
| 5,708,271 A | | 1/1998 | Ito et al. | |
| 5,954,206 A | * | 9/1999 | Mallon et al. | ............... 209/580 |
| 6,563,579 B1 | * | 5/2003 | Kimura et al. | ............... 356/246 |

FOREIGN PATENT DOCUMENTS

JP  6-288903  * 10/1994 .......... G01N/21/27

OTHER PUBLICATIONS

Patent Abstract of Japan JP 10015499, Jan. 20, 1998.
Patent Abstract of Japan JP 10202205, Aug. 4, 1998.
Patent Abstract of Japan JP 10048123, Feb. 20, 1998.
Patent Abstract of Japan JP 02218944, Aug. 31, 1990.

* cited by examiner

Primary Examiner—F. L. Evans
Assistant Examiner—Kara Geisel
(74) Attorney, Agent, or Firm—Reed Smith LLP

(57) ABSTRACT

An object of inside-quality inspection being conveyed on a conveyer is irradiated sideways with beams of light from projection lamps concentratedly. A photodetecting device detects light transmitted through the object irrespective of the size and thickness of the skin of the object without being influenced by extraneous light. A white-level calibrating device is provided to the photodetecting means. The projection lamps project and concentrate their beams of light onto one side of the object in an inspection position at different angles from different positions diagonally distributed from the oblique front to the oblique back. Fractions of light transmitted through the object and emerging from the other side of the object are condensed by a condenser lens A shutter for opening/closing the optical path is provided between a light receiving window of the condenser lens and a light-inputting face of an optical fiber for directing light to a spectrometer. The shutter is operated when the inspection center of the object passes the inspection position. A white-level calibrating plate is moved to a position in front of the light receiving window and moved back so as to perform calibration. The deviation of the calibration curve is corrected by placing a quality reference material in the same position and moving it back.

7 Claims, 10 Drawing Sheets

SIDE MULTIPLE-LAMP TYPE ON-LINE INSIDE QUALITY INSPECTING DEVICE

CROSS-REFERENCE TO RELATED APPLICATIONS

This application claims priority of PCT Application Serial No. PCT/JP00/04005, filed Jun. 20, 2000 and Japanese Application No. HEI 11-173916, filed Jun. 21, 1999,the complete disclosures of which are hereby incorporated by reference.

FIELD OF THE INVENTION

This invention relates to an on-line inside-quality inspecting device for non-destructively inspecting and measuring the inside-qualities such as sugar forming degree, acidity, etc. of the objects of inspection, such as agricultural products, by projecting beams of light on each of the objects from one side of it and by receiving and spectrally analyzing, on the other side, the light transmitted through the object while these objects of inspection are in process of being conveyed by various transport means.

BACKGROUND ART

Known methods for measuring the inside-quality of agricultural products include a reflection light method and a transmission light method. In the reflection light method, information on the inside-quality is detected through a reflection light obtained from the agricultural product by projecting beams of light including near infrared rays on the agricultural product. In the transmission light method, information on the inside-quality is detected from light transmittance through the agricultural product of the light projected on the agricultural product.

As disclosed, for example, in Japanese Laid-Open Patent Application No. HE 6-300681,the reflection light method is arranged to be carried out by projecting beams of light including near infrared rays onto a measuring object and by detecting the information on the inside-quality of the object from light reflected by the object as a result of light projection. The method, therefore, permits use of receiving trays arranged in a conventional screening device as they are.

However, the inside-quality information obtainable by the reflection light method is limited to information on a peripheral part and a part near to it of the agricultural product where the projected light is received. Therefore, this method is not applicable to a fruit having a thick skin, although the method is applicable to a fruit having thin skin, such as peaches and pears. In other words, it has been a problem with this method that, in the event of a fruit having a thick skin, the reflection light obtained gives information only on the quality of a thick skin part but does not give any information on the edible flesh part of the fruit.

The applicant of the present patent application has developed and practicalized an inside-quality inspecting device of the transmission light method which is capable of detecting information on the inside-quality of citrus fruits (oranges), melons, watermelons, etc. having thick skin parts and the honey forming parts, or brown scarred parts existing deep inside of apples or the like. The device developed and practicalized by the applicant is arranged, as disclosed in Japanese Laid-Open Patent Applications No. HE 6-288903 and No. HE 10-202205,to use a transport conveyer having agricultural products receiving trays having receiving seats. Each of the receiving seats is provided with a transmitted light passage which vertically penetrates the central part of the seat. The device is thus arranged to have its light receiving part opposed to the lower side of the center part of the receiving tray, so that the device can be used only for the conveyer of the type using such receiving trays. It has been impossible to use the device in combination with any conveyer that is not using the receiving trays of the above-stated type.

Meanwhile, known inside-quality inspecting devices of the transmission light method include a device disclosed in Japanese Laid-Open Patent Application No. HEI 7-229840.In this device, one light-projecting lamp is arranged as a light source on one side of the transport path of a belt conveyer; a light receiving part is opposed to the light-projecting lamp and arranged on the other side of the transport path at a position where an optical path extends horizontally and rectilinearly across the transport path; light is projected sidewise on each agricultural product under inspection; and light which is transmitted through the agricultural product as a result of light projection is detected by the light receiving part. The device is thus arranged to detect the light sidewise transmitted through the agricultural product. However, since the device uses only one light-projecting lamp, the rays of light projected are limited in intensity and quantity. Therefore, in the case of agricultural products having thick skins, the transmitted light has been too weak for spectral analysis and errors in the results of the spectral analysis have degraded the accuracy of measurement.

Agricultural products are naturally grown products. Generally, the inside-quality, such as sugar content, acidity, degree of ripeness, etc. of each product is not uniform and varies according to its parts on the side of having sunlight or on the shadow side thereof. Measurement values obtained by projecting light from the single projecting lamp, therefore, greatly vary and fluctuate depending on the direction of light projection. It has been thus hardly possible to ensure the measuring accuracy of the inside-quality inspecting device. It has been another shortcoming of the device disclosed in the above-cited Japanese laid-open patent application that a large case is necessary for housing it because the device disclosed is arranged to have a diffraction grating directly connected to its light receiving part.

Further, according to the arrangement disclosed, the optical axis of the light-projecting lamp and the light converging axis of a condenser lens of the light receiving part are on one and the same line. Therefore, intense rays of light come to be straightly incident on the condenser lens to bring about some adverse effect on a spectral light receiving element when the optical axis is not blocked by the agricultural product. To prevent the spectral light receiving element from being affected by the intense rays of light under such a condition, a shutter is provided at a light-projecting port. The shutter is, however, arranged to be left open between front and rear agricultural products under the inside-quality inspection while they are in process of transport and is not to be closed and opened for each of them one by one. When the light is not necessary, such as at the time of a pause, the rays of light of the lamp are arranged to be blocked by means of a shutter solenoid. However, although the light from the light-projecting lamp can be thus blocked, fluctuations of ambient light coming into a dark room through the passage of the agricultural product are allowed to come in as they are through the condenser lens to cause the zero level (of a dark current) of the light receiving element. This has been a shortcoming of the device.

Another shortcoming of the device lies in the following point: In order to have the light penetrate through a thickskinned agricultural product such as oranges, melons, watermelons and the like, with a single lamp used, the lamp must be arranged to have a high degree of output. However, use of such a high-output lamp necessitates some lamp cooling means as it generates a high temperature. Besides, since the light is converged onto the agricultural product by means of a reflection mirror, the light converging part is heated to have such a high temperature exceeding 500 degrees, which has necessitated use of a heat resisting material and presented the hazard of fire. Further, the filament of the high-output lamp is large. The large filament of the lamp not only makes the light converging arrangement difficult but also has a short service life and cannot be used over a long period of time without lowering the illuminance of the lamp.

If the quantity (intensity) of the projection light is increased to have the transmission light sufficiently obtainable even from inspecting objects which do not readily transmit light, the operational amplifier of a spectral analyzer tends to overflow to make the spectral analysis impossible for inspecting objects which readily transmit the projection light.

Further, the operating state of an on-line inside-quality inspecting device varies with variations in the temperature of the environment taking place at different times of the day, including the morning, noon and evening of the day, and also with the lapse of the operating time. Therefore, in order to stably operate the device over a long period of time, the device must be constantly calibrated. In the case of the above-stated prior art device, however, the light-projecting lamp and the light receiving part are arranged on one and the same optical axis in a state of being opposed to each other. With the device arranged in this manner, it has been impossible to stably carry out such calibration work in cases where the device is set within an imperfect dark room.

It has been a further shortcoming of the device that a calibration curve of the device tends to be caused to deviate by the variations of environment temperature and the lapse of operation time.

This invention is directed to the solution of the problems presented by the prior art device.

OBJECT AND SUMMARY OF THE INVENTION

It is therefore an object of this invention to provide an inspecting device having a light-projecting part and a light receiving part arranged to be opposed to each other across a transport path of a transport conveyer conveying agricultural products or the like and to permit use of conveyers of varied kinds without limiting the kind of the transport conveyers usable in combination with the inspecting device. In the device, the light-projecting part is arranged to project light onto a wide area of each agricultural product in an increased light quantity across the transport path without much decreasing the illuminance of light over a long period of time, so that the light transmitted to the light receiving part through the product can be efficiently detected irrespective of the degree of light transmissibility of the agricultural object (inspecting object) which varies with the size and kind of the object. It is another object of this invention to provide an inspecting device which includes overflow preventing means for preventing an operational amplifier from overflowing in the event of an inspecting object not allowing the projected light to be readily transmitted therethrough; a light receiving part and calibration means arranged to be not readily affected by disturbance light; and correction means for correcting the deviations of a calibration curve caused by deterioration due to aging, etc., so that inside-quality of the object can be inspected and measured in a highly accurate and reliable manner.

To attain the above-stated objects, this invention is characterized as described below:

In an inside-quality inspecting device according to this invention, light-projecting means is set on one side of the transport path of a transport conveyer which conveys objects of inspection one by one while light receiving means is set on the other side of the transport path and opposed to the light-projecting means across the transport path. Light is projected on each inspecting object from one side thereof while the object is in process of transport. The inside-quality of the object is then inspected by receiving the light transmitted through the inside of the object and coming out from the other side thereof and by performing spectral analysis on the light transmitted. The device according to this invention is characterized in that the light-projecting means is arranged to use a plurality of light-projecting lamps and to concentratedly project beams of light obliquely on each inspecting object, from different positions and at different angles covering a wide range of the surface areas on one side of the object from an obliquely front are to an obliquely rear area when the object is at an inspecting position on the transport path; and the light receiving means is provided with a light passage opening-and-closing mechanism in which a shutter is arranged to open and close the passage of light between a light receiving window of a condenser lens and a light inputting face of an optical fiber which is arranged to lead light to a spectroscope.

According to this invention, the beams of light are concentratedly and almost. uniformly projected over the whole surface of the inspecting object on one side thereof by using many lamps while the object is in the position to be inspected. Therefore, a large quantity of light can be projected from the many lamps to cover a large area on both the sunny side of the object where the object has sufficiently basked in the sunlight and the shadow side of it where it has not sufficiently had the sunlight even in the case where the sugar content is unevenly distributed to the sunny and shadow sides. As a result, the light transmitted through the various internal parts of the inspecting object carries averaged information on the internal quality of it when the transmitted light exits on the exit side of the object. The transmitted light is received and subjected to spectral analysis made by the light receiving means, so that the internal quality of the inspecting object can be adequately inspected.

The shutter disposed between the light receiving window of the transmitted-light-receiving condenser lens and the light inputting face of the optical fiber is arranged to be left closed when the inspecting object on the move comes to the fore end and the rear end of an inspection part of the transport path in the direction of travel. With the shutter arranged in this manner, the light transmitted can be unpitied to the light receiving means only from the central part of the object. In case where there is no inspecting object, the shutter remains closed to allow no light to enter into the spectral analyzer, so that the analyzer can be prevented from being affected by an increase in temperature.

An inside-quality inspecting device arranged according to this invention is characterized in that the condenser lens of the light receiving means is provided with a lens hood for securing a visual field in front of the condenser lens on the objective side thereof; a light receiving window which has a dust-proof structure with a transparent glass part arranged in front of the lens hood; and means for moving a white level calibration plate back and forth in front of the light receiving window for calibration.

According to the inventive arrangement, the condenser lens is provided with the lens hood which opens toward the center of the inspecting object to prevent an adverse effect of disturbance light and the light receiving window which restricts a visual field to a size which has only the transmitted light coming from the front of the condenser lens. The white level calibrating plate which comes to or retreats from the front of the light receiving window is arranged to permit calibration work on the overall output value of the device, before the start of operation, at a pause of the operation or after a pause of operation, to avoid such errors that might be caused by variations of environment temperature and deteriorations of lamps and the optical system of the device.

An inside-quality inspecting device arranged according to this invention is characterized in that the device is provided with an orifice plate. The orifice plate is arranged within the above-stated lens hood of the condenser lens to restrict and define a light passage area in such a way as to have the light receiving optical axis of the optical system at the center of the light passage area, so that scattering light and flares can be prevented from taking place.

The above-stated inspecting device according to this invention effectively removes all lights other than the light transmitted through the inspecting object, such as disturbance light and flares caused by scattering light entering into the lens hood from the light receiving window of the condenser lens and by irregular surface reflection taking place inside of the lens hood. The arrangement thus enhances the accuracy and reliability of the results of the spectral analysis.

An inside-quality inspecting device according to this invention is characterized in that the inventive device is provided with air cooling means. The air cooling means has a cooling air blowing duct and an air nozzle which blows cooling air toward the lens hood of the condenser lens and the white level calibrating plate in its stand-by position. The air cooling means is thus arranged to discharge heat caused by the rays of light coming from the light-projecting lamps to the condenser lens and the white level calibrating plate by blowing air from an air blower into the air blowing duct.

According to the above-stated arrangement, a gradual increase of temperature due to the beams of light from the light-projecting lamps can be suppressed to prevent the optical characteristics of the device from varying due to changes of temperature, so that the stability of results of spectral analysis can be maintained.

An inspecting device according to this invention is characterized in that, in the inventive device, each of the plurality of light-projecting lamps is provided with a reflecting mirror having a parabolic surface arranged to form a beam angle at which a focal point is obtained where the inspecting object is at its inspecting position. The front side of each of the lamps is sealed with a heat resisting glass part. These sealed lamps are arranged to have their light-projecting axes deviate from each other at such angles and positions that beams of light passing through the focal point do not rectilinearly come into the light receiving optical axis of the condenser lens of the light receiving means.

According to this invention, the plurality of light-projecting lamps are arranged to concentratedly project beams of light with their focal points located at the object position. This arrangement permits efficient use of relatively small lamps. Each light-projecting lamp has a sealed front, which acts to keep the reflecting power of the reflecting mirror not decreasing. The optical axes of the light-projecting lamps are arranged to deviate from each other at such angles that cause their beams of light not to rectilinearly enter into the light receiving optical axis of the condenser lens. By virtue of that arrangement, the device is not affected by any light that straightly passes through the inside of the inspecting object without diffusing inside of the object.

An inspecting device according to this invention as further defined in accordance with the invention is characterized in that each of the plurality of light-projecting lamps is provided with air cooling means. The air cooling means includes a cooling air blowing duct and an air nozzle which are arranged to send air to a sealed part inserted into a socket at each of the light-projecting lamps to prevent overheat by dissipating heat generated by the lamp body.

With the cooling means arranged in this manner according to this invention, each of the lamps which is in a state of having its front side sealed is air cooled by applying air from the nozzle to the sealed part. The arrangement thus effectively prevents overheat to make the service lives of the light-projecting lamps longer.

An inspecting device according to this invention is also characterized in that the plurality of light-projecting lamps are provided with projecting light quantity adjusting means for increasing or decreasing the number of lamps to be lighted up in such a way as to increase or decrease the quantity of light to be projected according to the size, item, kind and rate of light transmission of the inspecting object.

With the device arranged to include the projecting light quantity adjusting means, as mentioned above, the number of light-projecting lamps to be lighted up for inspection can be changed according to the item, kind and difference in rate of light transmission (size) of the inspecting object. The arrangement makes the device applicable to many items of inspecting objects including, for example, watermelons and melons which have thick skins and do not readily allow the inspection light to be transmitted through the inside of them; oranges which have a medium thickness of skin; tomatoes and pears which have thin skins to readily transmit light; apples; peaches; and so forth.

An inspecting device according to this invention is further characterized in that the device is provided with lifting-and-lowering means, by which a lamp box containing therein the plurality of light-projecting lamps of the light-projecting means is caused to be vertically moved upward or downward by remote control, so that the light-projecting height of the lamps can be adjusted by remote control according to the size of the inspecting object which varies with the item and kind thereof With the inside-quality inspecting device arranged to include the lifting-and-lowering means, the inspecting object can be easily and promptly switched from one over to another among different items and kinds of inspecting objects having different sizes. This arrangement is a great advantage in cases where the device must be used f or many different items as it facilitates stepwise change-over from one object to another.

An inspecting device according to this invention is still further characterized in that the light receiving means of the device defined is provided with filter change-over inserting means. The filter change-over inserting means is arranged to be operated to reduce the quantity of light incident on the optical fiber by selectively inserting any of light reducing filters of different kinds into the passage of light between the light receiving window of the condenser lens and the light inputting face of the optical fiber.

With the inside-quality inspecting device arranged in the above-stated manner according to this invention, even where the amplification degree of the operational amplifier of the spectral analyzer has been adjusted for such an inspecting object that allows only a small quantity of transmitted light to enter the light receiving means, the operational amplifier can be prevented from overflowing to hinder the spectral analysis by reducing and limiting the incoming light by means of the light reducing filter when the object giving a small quantity of transmitted light is changed over to an object which gives a large quantity of transmitted light.

An inspecting device according to this invention is also characterized in that the device having the light-reducing-filter change-over inserting means is provided with remote control change-over means for selectively operating by remote control a light-reducing-filter mounting plate on which a plurality of light reducing filters of different light reducing rates are mounted.

With the device arranged in this manner according to this invention, the stepwise change-over action on the light reducing filters can be easily carried out in a very short period of time when the object of inspection is changed from one kind over to another.

An inspecting device according to this invention is further characterized in that the shutter disposed between the light converging window of the condenser lens and the light inputting face of the optical fiber is arranged within a dark box which contains the passage of light and has its surrounding part tightly sealed. The shutter is thus arranged to be opened and closed for each of the inspecting objects one by one every time the object comes to pass the inspecting device. In other words, the shutter is operated to be opened when the inspecting object is in the inspecting position and to be closed to allow no light to come into the spectroscope when the inspection is not required.

With the invented device arranged in this manner, the spectroscope (spectral analyzer) is kept shielded from light except when the transmitted light is allowed to enter the center part of the inspecting object in the inspecting position. Since no light is allowed to come into the spectroscope to prevent it from being affected by a rise of temperature or the like, the zero level of the light receiving element of the device stably remains constant. The light receiving element always rises from its zero level to give a reliable inspection output every time an inspecting object is inspected.

An inspecting device according to this invention is still further characterized in that the shutter disposed between the light converging window of the condenser lens and the light inputting face of the optical fiber is arranged within a dark box which contains the passage of light and is shielded from its surroundings. The shutter is provided with shutter driving means which is arranged to have the shutter normally open and closed only when a dark level detecting action is performed before or after the white level calibrating plate is operated. The control circuit of a detecting light receiving element disposed on the rear side of the spectroscope is provided with an electronic shutter circuit, which is arranged to cause an electronic shutter to act every time one inspecting object passes the inspecting device.

The electronic shutter circuit which is included in the control circuit of the light receiving element on the rear side of the spectroscope is arranged to electrically perform time control over detection of light transmitted through each of inspecting objects in such a way as to discharge and clear the electric charge of detection. The electronic shutter thus operates without being affected by any residual detection electric charge obtained immediately before the detection. Since the electronic shutter circuit requires no mechanical moving part, the inspecting device can be continuously operated at a high speed so that the processing capability of the device per unit time can be enhanced by increasing the speed of the transport conveyer.

An inspecting device according to this invention is also characterized in that the device is provided with a mechanism for moving a quality reference material forward and backward in place of the white level calibrating plate, before or after the latter is moved forward and backward, in front of the light receiving window of the condenser lens of the light receiving means having the lens hood. The quality-reference-material moving mechanism is used as means for correcting aging fluctuations of the calibration curve of the spectral analyzer on the basis of variations taking place in light transmitted through the quality reference material.

In the inspecting device arranged according to this invention as mentioned above, light transmitted through a vessel which contains therein the quality reference material is detected in association with the calibration work performed with the white level calibrating plate. Then, aging fluctuations and variations of the calibration curve due to continuous lighting, continuous operation or the like of the inside-quality inspecting device and changes in the ambient temperature and environmental conditions of the device can be adequately corrected on the basis of the transmitted light thus obtained through the quality-reference-material containing vessel.

An inspecting device according to this invention is also characterized in that the mechanism for moving the quality reference material forward and backward is arranged to selectively move a plurality of quality reference materials by inching them one by one.

In carrying out component analysis for a plurality of components in respect to the sugar forming degree, the acidity, etc. of the inspecting object, the above-stated arrangement according to this invention permits correction of aging variations of the calibrating curve in accordance with the actual situation.

An inspecting device according to this invention is also characterized in that the quality reference material is a solid material.

According to this invention, a solid material having an absorbing characteristic in a wavelength band close to that of the inspecting object is employed as the quality reference material. The use of such a material permits calibration work stably performed as it little deteriorates even when it is used over a long period of time.

An inspecting device according to this invention is characterized in that the quality reference material is a liquid material contained in a vessel.

According to this invention, a liquid material having a quality component equal to that of the inspecting object is employed as the quality reference material. Such a liquid material can be easily obtained, so that the calibration work can be carried out in accordance with the actual situation.

An inspecting device according to this invention is further characterized in that the device is provided with lifting-and-lowering means for vertically moving the mount base of the light receiving means by remote control. The lifting-and-lowering means is arranged to permit adjustment of the height of a light receiving optical axis by remote control according to the size of the inspecting object which varies with the item and kind of the inspecting object.

By virtue of the arrangement according to this invention, the inspecting object can be easily and promptly switched from one over to another among different items and kinds of inspecting objects having different sizes.

DESCRIPTION OF THE PREFERRED EMBODIMENTS

Figure 1:
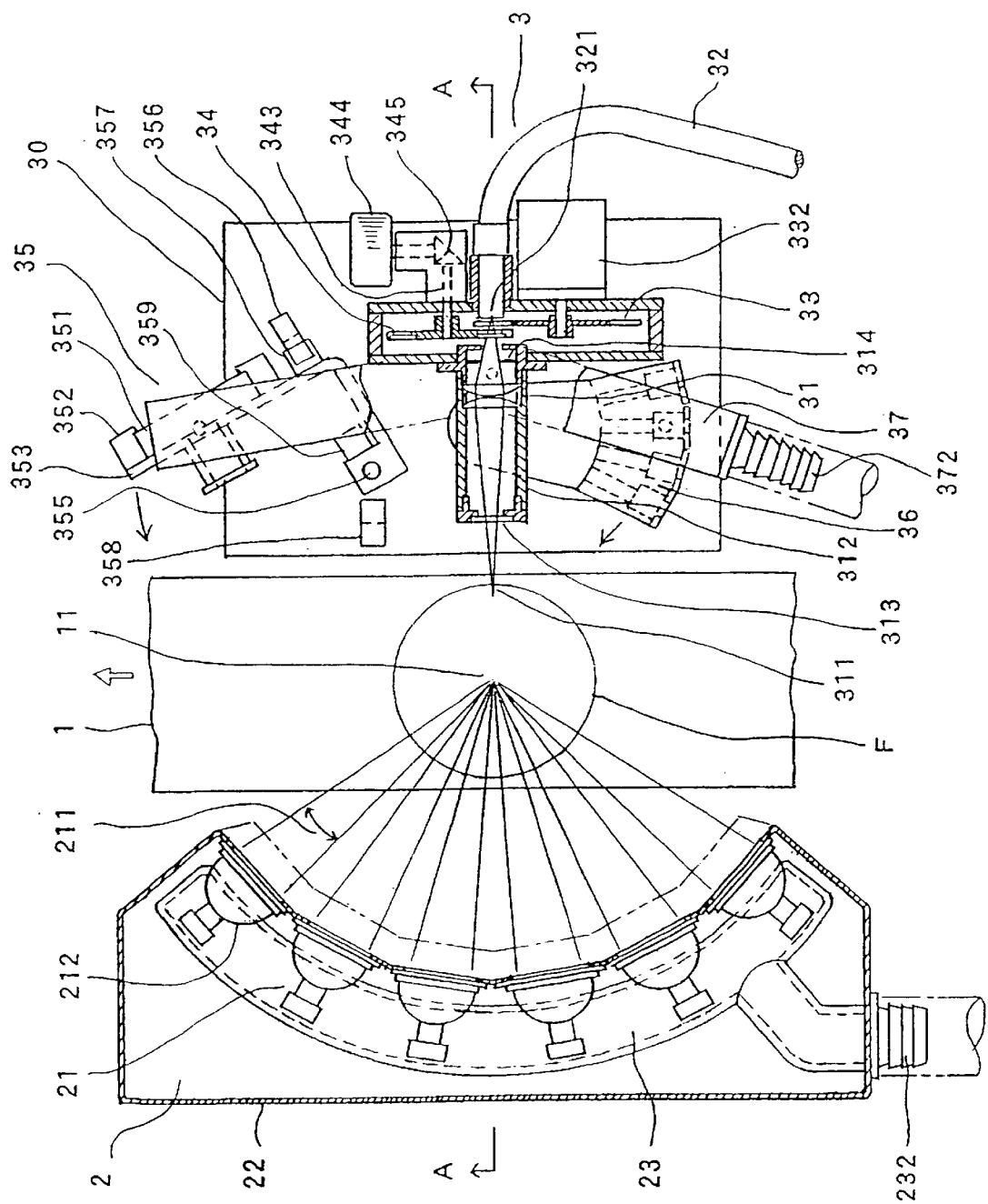
FIG. 1 is a plan view of an embodiment of the inside-quality inspecting device according to this invention, including a sectional view of the essential parts of light-projecting means and those of light receiving means of the device arranged across a transport path.

In accordance with this invention, a side multi-lamp type on-line inside-quality inspecting device is arranged as follows: In the device, light-projecting means and light receiving means are arranged across a transport path of a transport conveyer which conveys inspecting objects one by one. The light-projecting means includes a plurality of light-projecting lamps which are arranged on one side of the transport path to concentratedly project beams of light onto the object at different angles and from different positions located in a range spreading from an obliquely front part to an obliquely rear part with respect to the surface of the object on this side. The light receiving means is arranged on the other side of the transport path and includes a shutter. The shutter is disposed between a light receiving window of a condenser lens which converges light transmitted through the inspecting object and a light inputting face of an optical fiber which leads the convergent transmitted light to a spectroscope. The shutter is thus arranged to open and close a passage of light leading to the spectroscope. The light receiving window is open toward the inspecting object when the object is in a position to be inspected. When the center of the inspecting object where the object is to be inspected comes to an inspecting position, the shutter opens to allow light transmitted through the center to come to the spectroscope through the optical fiber. In other words, the center part of the object is an inspecting part of the inspecting object and does not have to be a dimensional center of the object.

The shutter is closed to shut off the passage of the transmitted light to allow no transmitted light from the condenser lens to come into the spectroscope through the optical fiber when there is no inspecting object or when the fore end part or the rear end part of the object is at the inspecting position. In other words, unnecessary rays of light are not allowed to come into the spectroscope to effectively prevent environmental changes from having adverse effects such as a rise of temperature inside of the spectroscope.

The condenser lens is preferably arranged to have its objective-side focal point at a peripheral surface area of the object on the side of the lens. The condenser lens is provided with a lens hood which is arranged in front of the objective side of the lens to have a visual field toward the center of the object and with a dust-proof light receiving window which has a transparent glass on its front side. With the condenser lens arranged in this manner, the light can be effectively converged by preventing the adverse effect of disturbance light.

Inspecting objects on the transport conveyer are aligned by a process performed before the inspecting position to have the peripheral side surface of each of them at a fixed distance from the lens side of the light receiving means, irrespective of difference in size of them. With the inspecting objects on the move aligned on one side in this manner, the transmitted light converging condition becomes unvarying to enhance the reliability of the spectral analysis by minimizing errors.

Further, there is arranged means for moving a white level calibrating plate, with a mounting arm, forward and backward in such a way as to close and open the visual field in front of the light receiving window of the lens hood. The mounting arm is preferably provided with a tubular protruding part which extends from a white-level-calibrating-plate mount part toward the front of the lens hood in such a way as to encircle and shield the visual field from its surroundings. With the tubular protruding part formed in this manner, a calibrating action can be adequately carried out without being affected by any disturbance light. The white level calibrating plate is arranged to be at the objective-side focal point near to the peripheral side face of the inspecting object on the lens side. Variations in temperature of the environment necessitates calibration, for example, at a start or after a pause of operation of the inside-quality inspecting device. In such a case, the white-level-calibrating-plate moving means is operated to calibrate the device by moving the white balance level calibrating plate to the front of the lens-hood light receiving window either when no inspecting object is being conveyed or by suspending the transport operation of the conveyer. The calibration enables the inspecting device to be stably used over a long period of time. In inspecting the inside-quality of each inspecting object by converging light transmitted through the object while the object is on the move, the white level calibrating plate is retracted to a stand-by position away from a transport passage to prevent it from hindering the transport.

An optimum direction in which the white level calibrating plate is to be retracted to the stand-by position is determined in relation to the arrangement of the transport conveyer. The white level calibrating plate is, however, arranged to be retracted to a position which is located either outside of the transport passage in the forward traveling direction of the transport passage or upper outside of it.

An orifice plate is arranged inside of the lens hood to restrict the area of passage of the transmitted light. The provision of the orifice plate effectively prevents the flare of any scattered light coming from the light receiving window or any harmful reflection light obtained within the lens hood.

An air nozzle is provided for cooling with air the lens hood and the white level calibrating plate when it is in the stand-by position outside of the visual field. A cooling air blower is arranged to blow cooling air at the lens hood and the white level calibrating plate through the air nozzle. This arrangement effectively dissipates heat due to rays of light to minimize fluctuations of optical characteristics for a stable operation.

Each of a plurality of light-projecting lamps is provided with paraboloidal reflecting mirror to form such a beam angle that gives focal point at the center of the inspecting object. The light-projecting lamps are sealed lamps having sealed fronts and arranged to project beams of light concentratedly on the inspecting object. The arrangement permits use of small lamps as the beams of light can be efficiently projected. The sealed fronts of these lamps enables the reflecting mirrors to maintain a sufficient reflecting power by preventing them from having dust thereon and from becoming frosty.

Further, the light-projecting lamps are arranged to have their light-projecting optical axes deviate from each other at such angles and positions that their beams of light do not rectilinearly come into the optical axis of the condenser lens of the light receiving means. By virtue of this arrangement, the light which is diffused and transmitted through the inside of the inspecting object can be obtained in such a state that effectively gives a large amount of internal quality information.

The light-projecting lamps are preferably provided with a lamp box having lamp mount parts arranged therein in such a way as to enable the light-projecting lamps to project equal quantities of light from equal distances within a range from an obliquely front part to an obliquely rear part on one side of the inspecting object when the object is in the inspecting position. The light-projecting lamps are provided further with air blowing nozzles which are arranged to blow cooling air from an air blower to the sealed parts of the lamps to dissipate heat generated by the lamp bodies, so that the service lives of the lamps can be lengthened.

A control circuit is arranged to cause the plurality of light-projecting lamps to light up, for example, to a full degree, to a four quarter degree, to a three quarter degree or to some other suitable degree. With the device provided with such a control circuit, the lighting degree can be selected according to the size, item and kind of the inspecting object. The lighting degree is decreased in cases where the light transmitted through the object is too intensive and decreased where the transmitted light is too weak by easily changing the lighting degree from one degree over to another.

The plurality of light-projecting lamps are arranged to be vertically movable together with the lamp box upward or downward by a remote control operation according to the position of the center of the inspecting object, that is, when the inspecting object is switched from one object over to another object having a different size. That arrangement permits switch-over of the inspecting objects to be promptly carried out.

The inside-quality inspecting device may be provided with a light-reducing-filter selectively inserting mechanism as another light reducing means. The inserting mechanism is arranged to reduce the quantity of a transmitted light input to the spectroscope by selectively inserting light reducing filters of different light reducing rates into the received transmitted light passage of the light receiving means. The light-reducing-filter selectively inserting mechanism may be arranged to be operated by remote control. Such arrangement further shortens the length of time required in switching the inspecting object from one kind (or item) over to another.

The above-stated shutter is disposed within a dark box which is sealed including therein the surroundings of an optical path arranged to lead the light transmitted through the object from the condenser lens to the spectroscope. The shutter is thus arranged to normally close to prevent disturbance light and to open to lead the transmitted light to the spectroscope only when the center part of the object comes to the front of the condenser lens every time one inspecting object passes the inspecting device. The shutter is thus arranged to allow only the light transmitted with the inspecting object in the inspecting position to come into the spectroscope and to allow no other rays of light to enter the spectroscope in such a way as to allow a light receiving element disposed inside of the spectroscope to build up always from a zero level.

Further, in cases where the device is required to have such a high speed performance that is hardly attainable by mechanical means, the shutter which is disposed within the sealed dark box including the surroundings of the optical path from the condenser lens to the spectroscope is arranged to be driven by driving means to be normally open and to close only in detecting a dark level for calibration before or after the operation of the white level calibrating plate; and the control circuit of a detection light receiving element disposed in the rear of the spectroscope is arranged to have an electronic shutter circuit. In this case, each of the inspecting objects is inspected by detecting the transmitted light under the time control of electrical means. In other words, in cases where a high speed performance is required for time control for each object, an electronic shutter which is arranged to electrically perform the time control is used in combination with the mechanical shutter which does not have to be frequently operated and is arranged to mechanically shut off the light passage only in detecting the dark level.

A mounting arm is arranged to protrude and retract, in place of the white level calibrating plate, a reference material (substance) to and from the front, of the light receiving window of the condenser lens which is provided with the dust-proof lens hood. The reference material to be mounted on the mounting arm is selected from among materials which are similar or equivalent to the inspecting object in respect of transmitted light component. For mounting it, each reference material is arranged to have a holder, if it is a solid, or to be placed inside of a vessel if it is a liquid of sugar or acid. With the reference material thus mounted, any change due to the aging of a calibration curve is corrected in such a manner that the result of analysis made by a spectral analyzer on light transmitted through the reference material and led to the spectroscope is always the same as the result of analysis obtained when calibration is made the last time.

In the case where a plurality of vessels containing sugar or acid reference materials are arranged, the aging change of the calibration line is corrected by inching the reference-material-containing vessels one by one and by leading the transmitted light obtained through each of them to the spectroscope. Then, any aging change of the calibration curve is corrected in such a way as to make the result of analysis made by the spectral analyzer always unvarying with respect to one and the same reference material.

The condenser lens of the light receiving means and the mechanisms for protruding and retracting the white level calibrating plate and for protruding and retracting the reference material in relation to the condenser lens are arranged on one and the same mount base (frame). The mount base is provided with a mechanism which is arranged to be caused by remote control to vertically move the mount base upward and downward. The height of a light receiving optical axis is thus arranged to be adjustable by moving the mount base upward or downward according to the size of the inspecting object which varies depending on the item and kind of the inspecting object.

The lamp box of the light-projecting means and the light receiving means on the other side are preferably made of some vibration-proof rubber material. The use of such rubber material prevents the device from being affected by the vibrations of the transport conveyer to further lessen the errors of the spectral analysis.

EMBODIMENT 1

Figure 2:
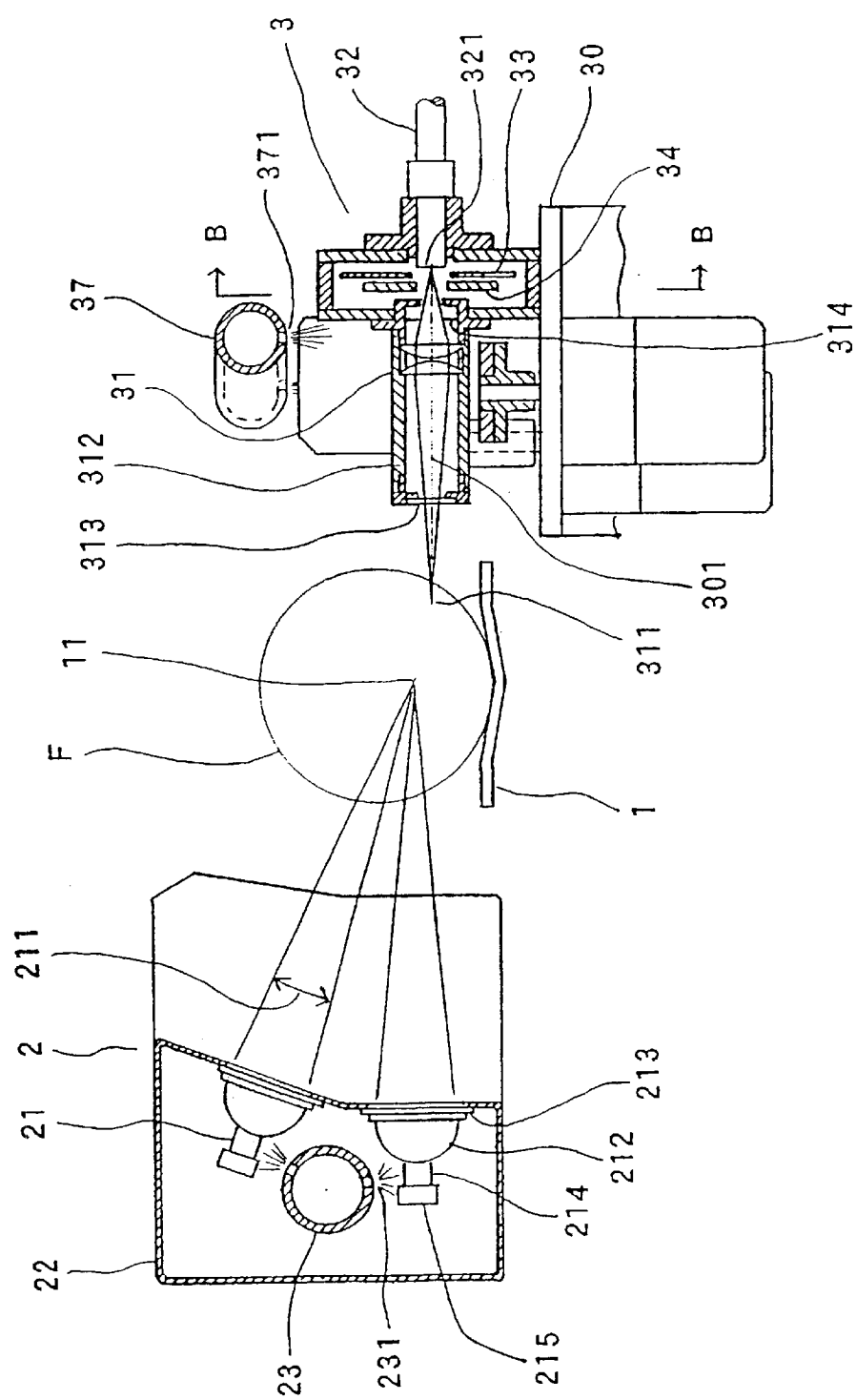
FIG. 2 is a side view of a vertical section taken along a line A—A shown in FIG. 1.

An inside-quality inspecting device which is arranged according to this invention as a first embodiment thereof is described with reference to FIGS. 1 to 8 as follows:

FIGS. 1 and 2 show in outline the essential parts of the on-line inside-quality inspecting device adapted for inspection of agricultural products. Referring to FIGS. 1 and 2, the illustrations include a transport conveyer 1 which is arranged to transport an inspecting object F. Light-projecting means 2 is arranged to project beams of light on the object F from on one side thereof. Light receiving means 3 is arranged to receive transmitted light obtained through the inside of the object F as a result of the light projection by the light-projecting means 2. The transport conveyer 1 is arranged to convey a row of inspecting objects F for inspecting inside-quality one by one. The transport conveyer 1 may be any of conveyers conventionally used for measuring the size or the appearance of agricultural products, such as a belt conveyer, a chain conveyer or a chain conveyer with receiving trays, so long as they are arranged to convey the inspecting objects F in a row in the traveling direction of them. In actually inspecting the inside-quality of each of the objects F, the grades of size and shape are also measured along with the inside-quality inspection in many cases. These measuring processes are arranged to be performed before or after the inside-quality inspection on the same transport conveyer. As shown in FIGS. 1 and 2, each inspecting object F conveyed by the transport conveyer 1 is in a state of having no obstacles on its two sides when it passes between the mount parts of the light-projecting means 2 and the light receiving means 3.

The light-projecting means 2 includes a plurality of light-projecting lamps 21. These lamps 21 are arranged and mounted on a lamp box 22 in such a way as to project beams of light on one side of the object (agricultural product) F to cover its range of surface area from an obliquely front area to an obliquely rear area when the object F is in an inspecting position. Each of the light-projecting lamps is relatively small in size and is provided with a paraboloidal reflecting mirror 212 which is arranged to form a beam angle 211 to give a focal point at the inspecting position 11. Each of these lamps is preferably a sealed halogen lamp and has its front sealed with a heat resistive sealing glass 213. Since the small lamps can be lighted up at a low voltage, the size of their filament can be reduced to enhance their light converging efficiency. In addition to that, use of a nichrome wire having a relatively large diameter effectively makes the service lives of the lamps longer. The light-projecting lamps 21 are arranged, as shown in FIGS. 1 and 2, in a configuration arcuately or radially spreading from an obliquely front point to an obliquely rear point on one side of the inspecting position 11. It is preferable that the lamps are equally spaced and arranged in a plurality of steps also in the vertical direction of the radial configuration. The light-projecting lamps 21 are mounted at such angles and positions that the beams of light passing through the focal point on the optical axis do not rectilinearly come into the light receiving optical axis 301 of a condenser lens 31 of the light receiving means 3. A cooling air blowing duct 23 for dissipating heat on the lamp side is arranged along the sealed parts 214 and the sockets of the light-projecting lamps 21. Heat generated from the sealed parts 214, the sockets 215 and the bodies of the lamps 21 is thus dissipated by blowing air from an air blower to prevent overheat. The air is blown from the air blower which is not shown by connecting suitable air blowing means to a connection port 232.

The light-projecting lamps are provided in a large number necessary for projecting light in a sufficiently large quantity to obtain a sufficiently large quantity of transmitted light from such an inspecting object that does not readily allow light to be transmitted therethrough. However, the electric circuit of the inspecting device includes means for increasing or decreasing the number of lamps to be lighted up according to the object. The number of lamps, therefore, can be reduced in inspecting an object through which light is readily transmitted, such as tomatoes or the like.

The light receiving means 3 includes, as main parts, a condenser lens 31; an optical fiber 32 which is arranged to lead convergent transmitted light to a spectroscope which is not shown (in the drawings); a shutter 33 which is arranged to shut up the light inputting face of the optical fiber 32; a light-reducing-filter mounting plate 34; a white level calibrator 35; and a quality-reference-material inserting (check) unit 36. These main parts of the light receiving means 3 are mounted, in combination, on a mount base 30. In the case of this embodiment, these main parts are mounted on 1 the upper side of the mount base 30. However, they may be arranged on the lower side of the mount base 30. The condenser lens 31 is arranged to have an objective-side focal point 311 on a peripheral surface of the object F when the object is in a center inspecting position on the transport conveyer 1. The condenser lens 31 is provided with a lens hood 312 which extends near to the object F; and a light receiving window 313 which has a transparent glass disposed in front of it. The lens hood 312 is arranged to ensure efficient input of such transmitted light that comes from the front part of a visual field which is defined by the light receiving window 313, so that the adverse effects of any undesirable incoming light such as disturbance light existing around the condenser lens 31 can be effectively prevented. An orifice plate 314 is arranged to prevent a harmful flare of scattering light coming from the light receiving window disposed between the condenser lens 31 and the filter mounting plate 34 within the lens hood 312 or that of reflection light within the lens hood 312. The optical fiber 32 is mounted with its light inputting face 321 adjusted to the image forming position of the condenser lens 31. The transmitted light which comes into the condenser lens 31 through the light receiving window 313 is imaged on the light inputting face 321 of the optical fiber 32 to be led by the optical fiber 32 to the spectroscope for spectral analysis.

Figure 8:
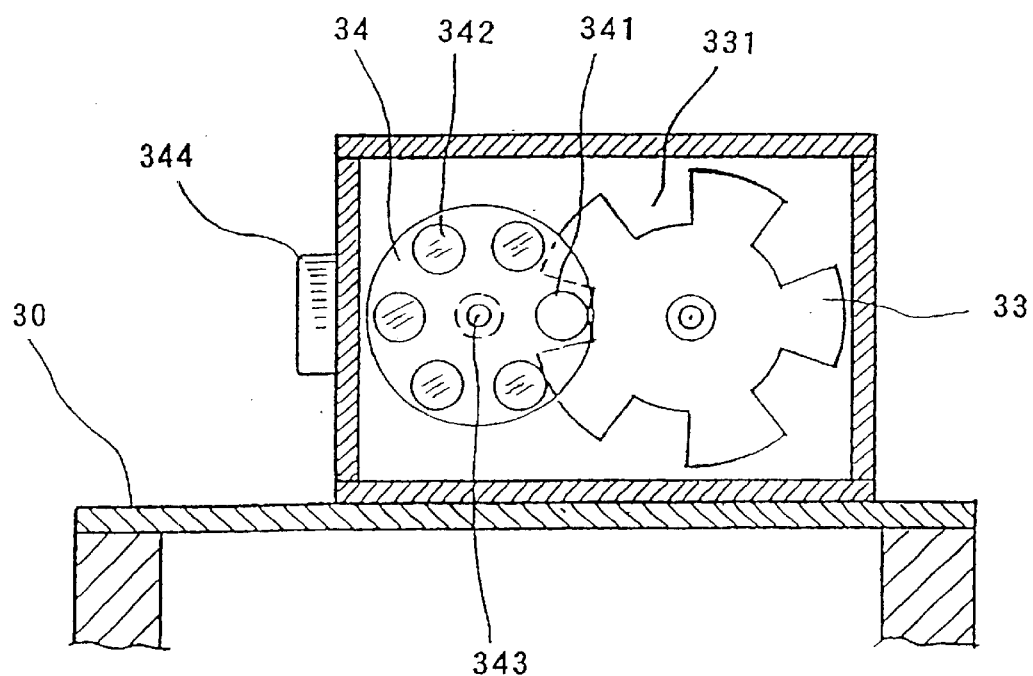
FIG. 8 shows the same part of the device as FIG. 7 as in a state obtained with the shutter opened.

The shutter 33 is arranged preferably near to the convergent transmitted light imaging position of the condenser lens 31, i.e. the light inputting face 321 of the optical fiber 32. The shutter 33 has a plurality of cutaway parts 331 formed and evenly spaced along the periphery of a disk, as shown in FIG. 8, and is arranged to open or close a light receiving optical path in front of the light inputting face 321 of the optical fiber 32.

More specifically, the shutter 33 is caused to open every time the center part of each object F passes the inspecting position 11 by a stepping drive unit 332 which is arranged to drive the shutter 33 in an inching manner for the object F one by one. With the shutter 33 opened in this manner, the transmitted light from the object F is passed through the optical fiber 32. The shutter 33 is caused to rotate to close in the inching manner by the stepping drive unit 332 when the inspecting part (the center part, for example) of the inspecting object F has passed away from the inspecting position 11. In other words, the shutter 33 is arranged to open to pass the transmitted light to the spectroscope at such timing that is adjusted to arrival at the inspecting position of the inspecting part (the center part) of the object F being randomly conveyed by the transport conveyer irrespective as to whether a plurality of inspecting objects are conveyed at regular intervals or at irregular intervals. However, when the fore and rear ends of object F is passing and during an interval time between one object and another, the shutter remains closed. In the case of this embodiment, the shutter 33 is thus arranged to remain open for inspecting the center part of the object F for a fixed period of the traveling time of the transport conveyer 1 and to remain closed for other parts of the object F, irrespective of the size of the object F. A command to operate the shutter 33 is arranged to be given by known means such as a shift signal or the like sent in synchronism with the transport conveyer 1 by detection means of one of varied kinds such as a camera, which is arranged on the upstream side of the transport conveyer 1 to measure the outside diameter, the color and the shape of the inspecting object F.

A light-reducing-filter mounting plate 34 has a plurality of filter mounting holes 341. One of the holes 341 is left blank while light reducing filters 342 of different light reducing rates are respectively placed in other holes. The filter mounting plate 34 is mounted on a shaft 343 in a position adjusted to the center of a light passage through which the received light passes between the condenser lens 31 and the light inputting face of the optical fiber 32. The holes 341 of the filter mounting plate 34 are selectively used by rotating the mounting shaft 343 through a miter gear 345 with a knob handle 344 which is disposed on the outside of the device. The light reducing filter selecting operation may be arranged to be performed by remote control, with a stepping motor or a like drive device provided, instead of using the knob handle 433.

The shutter 33 and the filter mounting plate 34 are arranged in a dark room which is encompassed with plates to prevent them from being affected by disturbance light.

Figure 3:
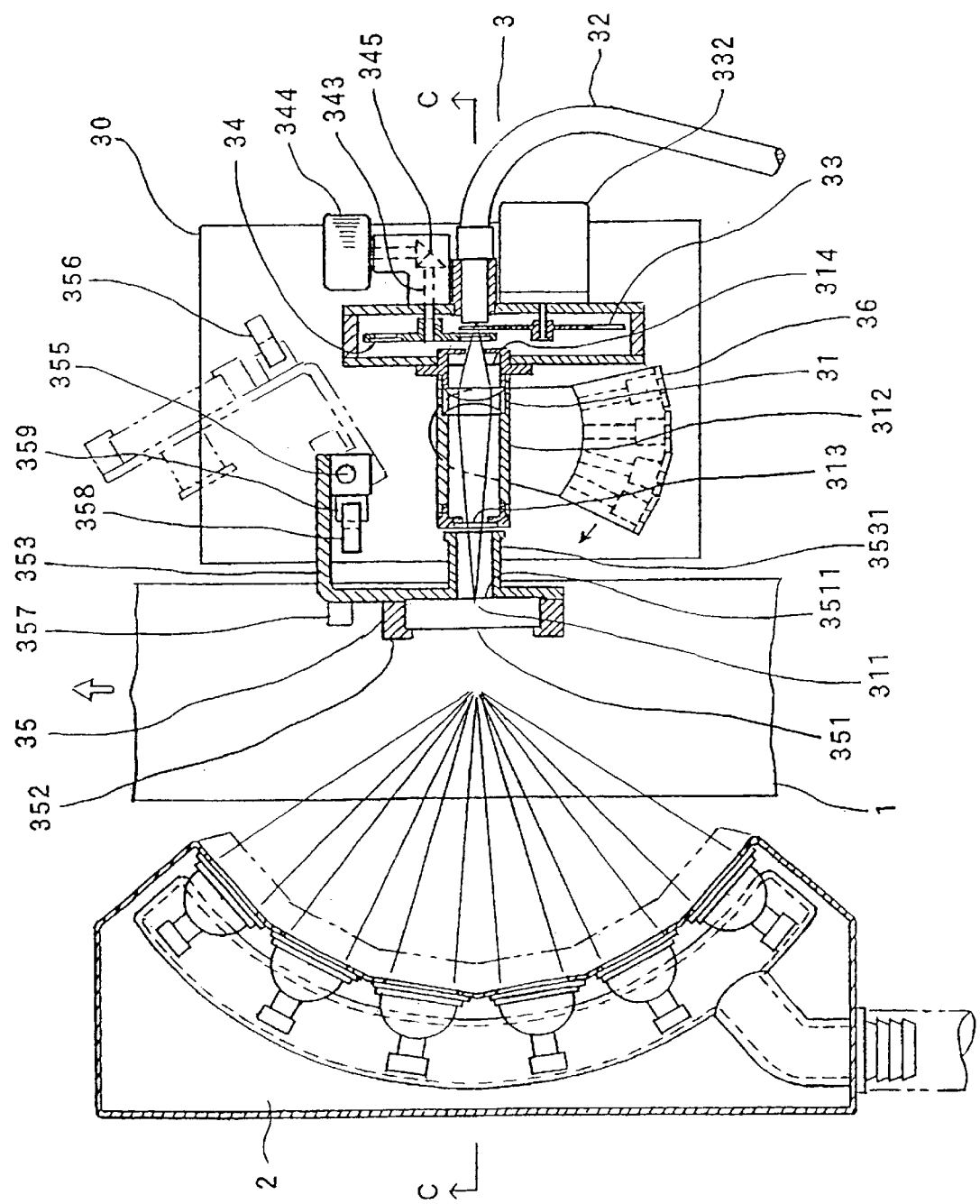
FIG. 3 is a plan view showing the operation of a white level calibrator of the light receiving means.
Figure 4:
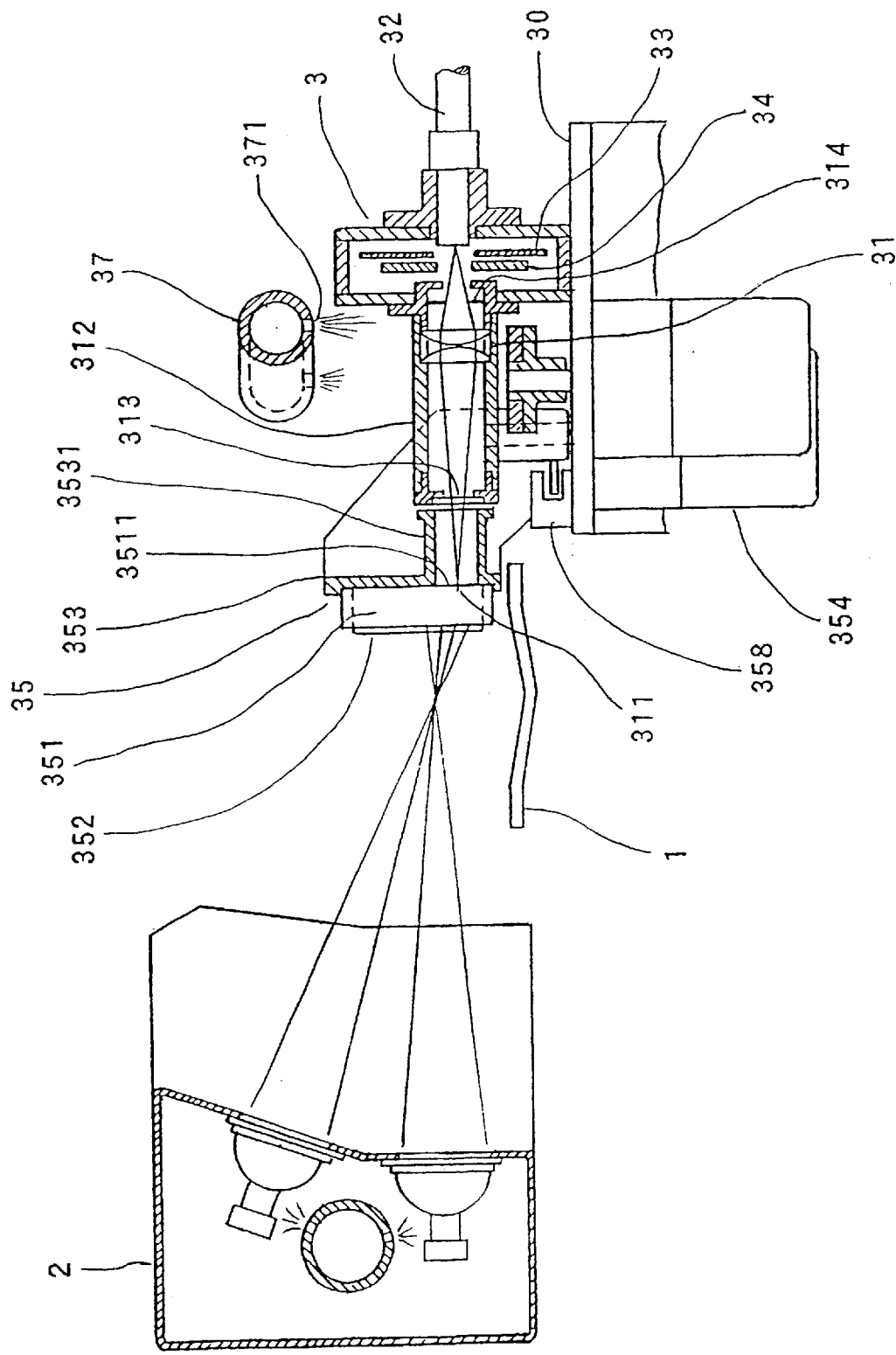
FIG. 4 is a side view of a vertical section taken along a line C—C shown in FIG. 3.

The white level calibrator 35 which has a white level calibrating plate 351 is shown in FIGS. 3 and 4 as in a calibrating action. The white level calibrator 35 is mounted on a mounting arm 353 with a retaining metal 352. The mounting arm 353 is mounted on a rotation shaft 355 protruding upward from a stepping motor R354 which is disposed below the mount base 30. For a calibrating operation, the stepping motor R354 is caused to make a normal rotation or a reverse rotation to bring the white level calibrating plate 351 forward in front of the light receiving window which is on the front side of the condenser lens 31 or to retract it from the transport path. The position of the peripheral face 3511 of the white level calibrating plate 351 which is in contact with the mounting arm 353 is adjusted to the objective side focal point 311 of the condenser lens. The mounting arm 353 is provided with a tubular projection 3531 which protrudes toward the lens hood 312 and serves to prevent any adverse effect of disturbance light that might come into the light receiving window 313 from between the white level calibrating plate 351 and the light receiving window 313. A detection switch 356 is arranged to detect that the mounting arm 353 is in its stand-by position by means of a detection piece 357.

A detection switch 358 is arranged to detect that the mounting arm 353 is in a position in front of the light receiving window of the condenser lens 313 to permit a calibrating operation. The detection switch 358 is provided with a detection piece 359 which is disposed at the mounting arm 353. A white level calibrating operation is performed with the white level calibrating plate 351 found by the detection switch 358 to be in a predetermined position in front of the condenser lens hood 312. The on-line inspecting device is actuated after the mounting arm 353 is found by the detection switch 356 to have been retracted from the transport path. These operations are automatically carried out respectively through a control circuit in accordance with operation commands.

Figure 5:
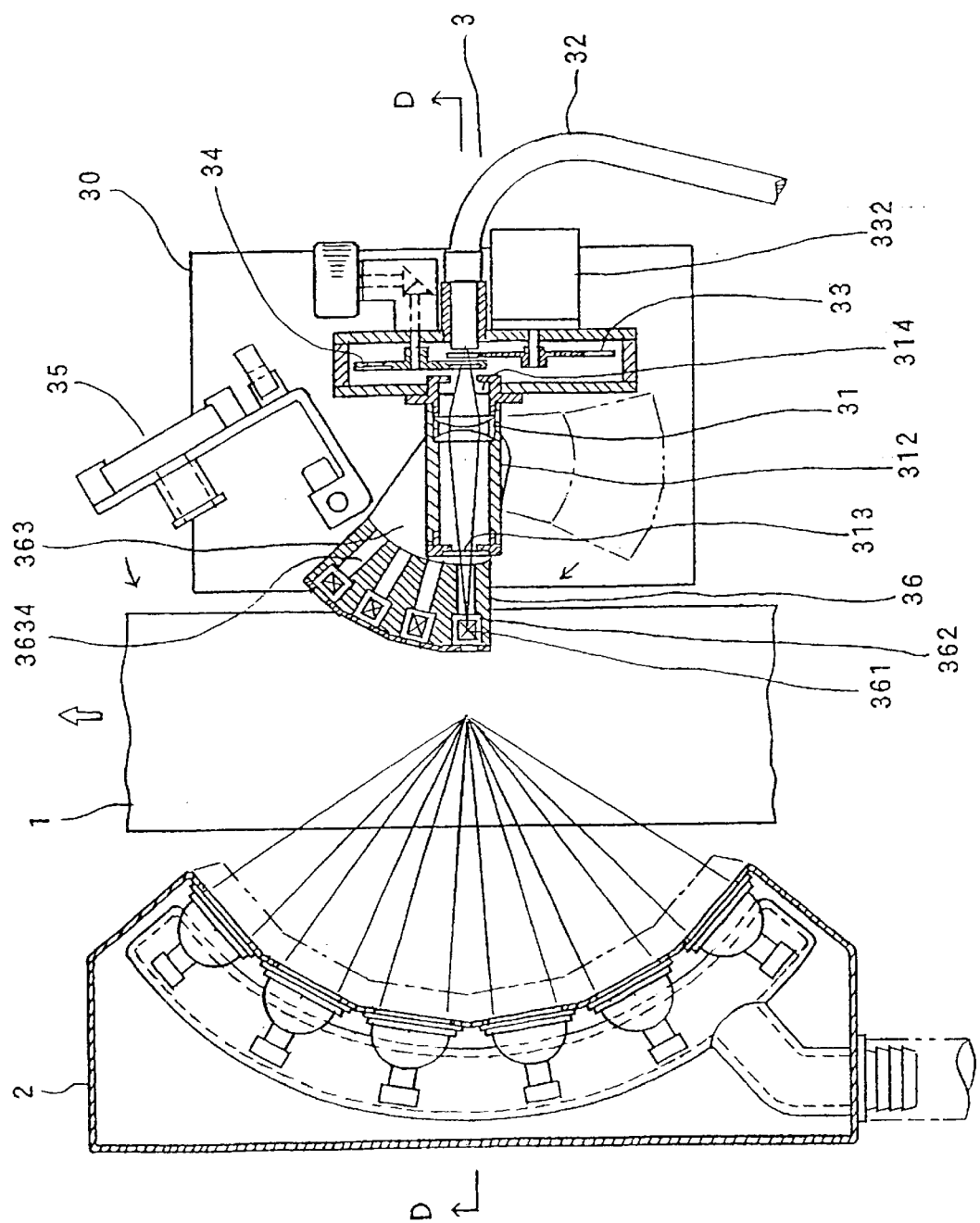
FIG. 5 is a plan view showing how vessels containing quality reference materials are operated on the side of the light receiving means.
Figure 6:
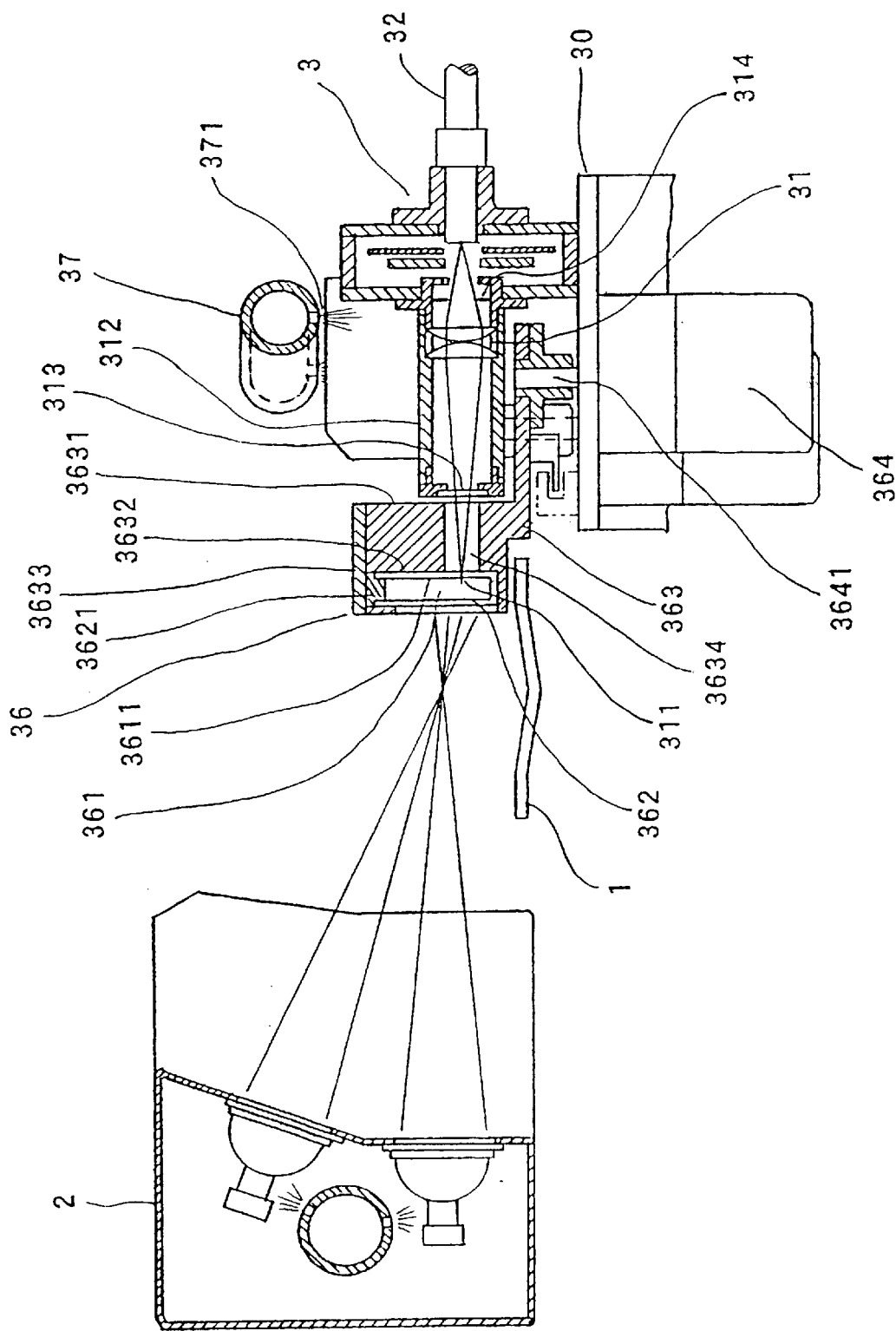
FIG. 6 is a side view of a vertical section taken along a line D—D shown in FIG. 5.
Figure 7:
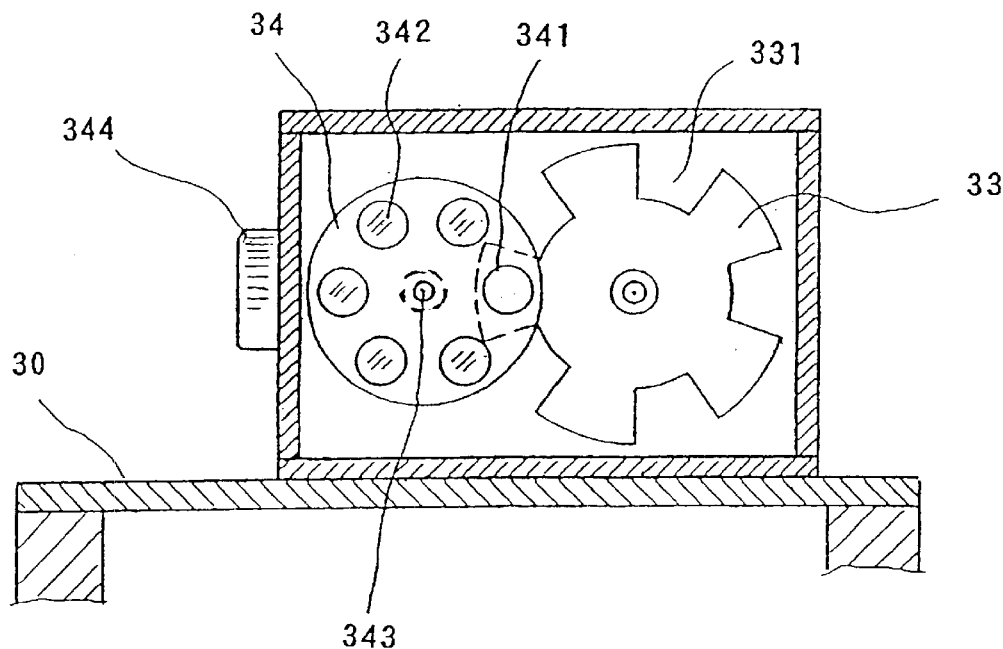
FIG. 7 is a vertical section taken along a line B—B of FIG. 2 showing a light reducing filter as in a state obtained with a shutter closed.

FIGS. 5 and 6 show the quality reference material check unit 36 as in a state obtained in making a check with a quality reference material 361. In the case of this embodiment, a plurality of quality reference materials 361 are prepared by placing solutions having a high degree of sugar, a low degree of sugar, a high degree of acidity and a low degree of acidity, respectively, in vessels 362 which are made of transparent quartz glass. With these solutions placed therein, the vessels 362 are plugged up with plugs 3621. Each of the quality reference material containing vessels 362 are loaded on a mounting arm 363, which is arranged to be capable of bringing each of these vessels 362 to the position of the objective side focal point 311 of the condenser lens 31. The mounting arm 363 consists of a sectoral light blocking wail part 3631 which arcuately spread to block light in front of the lens hood 312; a plurality of loading parts 3632 which are horizontally arranged side by side along the peripheral part of the light blocking wall part 3631 to receive the plurality of vessels 362; an upper retainer 3633; a peep hole 3634 which forms a passage for transmitted light between each of the loading parts 3632 and the lens hood 312; and an arm part which is arranged at a lower part of the mounting arm 363 to horizontally extend below the condenser lens 31. The arm part is mounted on the output shaft 3641 of a stepping motor S364. Each of the peep holes 3634 serves to prevent an adverse effect of disturbance light coming into the light receiving window when a weak transmitted light is led from the condenser lens to the optical fiber 32.

The quality reference material check unit 36 is used as necessary for correcting variations of a calibration curve of spectral analysis taking place after the white level calibration in cases where environment temperature or humidity have changed or where any changes happen to take place with the lapse of time.

This check unit 36 is retracted away from the locus of transport (transport path) of the transport conveyer 1 while the object F is in process of on-line inspection as shown in FIG. 1. In making a check, the check unit 36 is operated as follows: The stepping motor S364 is actuated to bring the loading part 3632 and the peep hole 3634 of each of the reference material containing vessels 362 to a position corresponding to the light receiving window 313 of the condenser lens 31 one after another. The light transmitted through each reference material and obtained from the peep hole 3634 is passed through the optical fiber 32 to be subjected to spectral analysis. Then the calibration curve is corrected according to the result of spectral analysis. A position confirming sensor or the like of any of varied kinds is arranged around the stepping motor S364 or its output shaft 3641 to find whether the mounting arm 363 is in the process of checking the quality reference material on the locus (path) of transport or is in its retracted position outside of the transport locus. The quality reference material 361 may be used in a liquid, gel or solid state.

The light receiving means is provided with a cooling air blowing duct 37. The duct 37 is provided with air blowing nozzles 371 which are arranged to blow cooling air of an air blower at the upper part of the lens hood 312 of the condenser lens 31, the upper part of the white level calibrating plate 351 which is retracted on one side of the lens hood 312 and the upper parts of the quality reference materials 361. Heat generated by rays of light is thus arranged to be dissipated. The cooling air blowing duct 37 can be arranged in any suitable shape to blow air at various parts of the light receiving means 3.

EMBODIMENT 2

Figure 9:
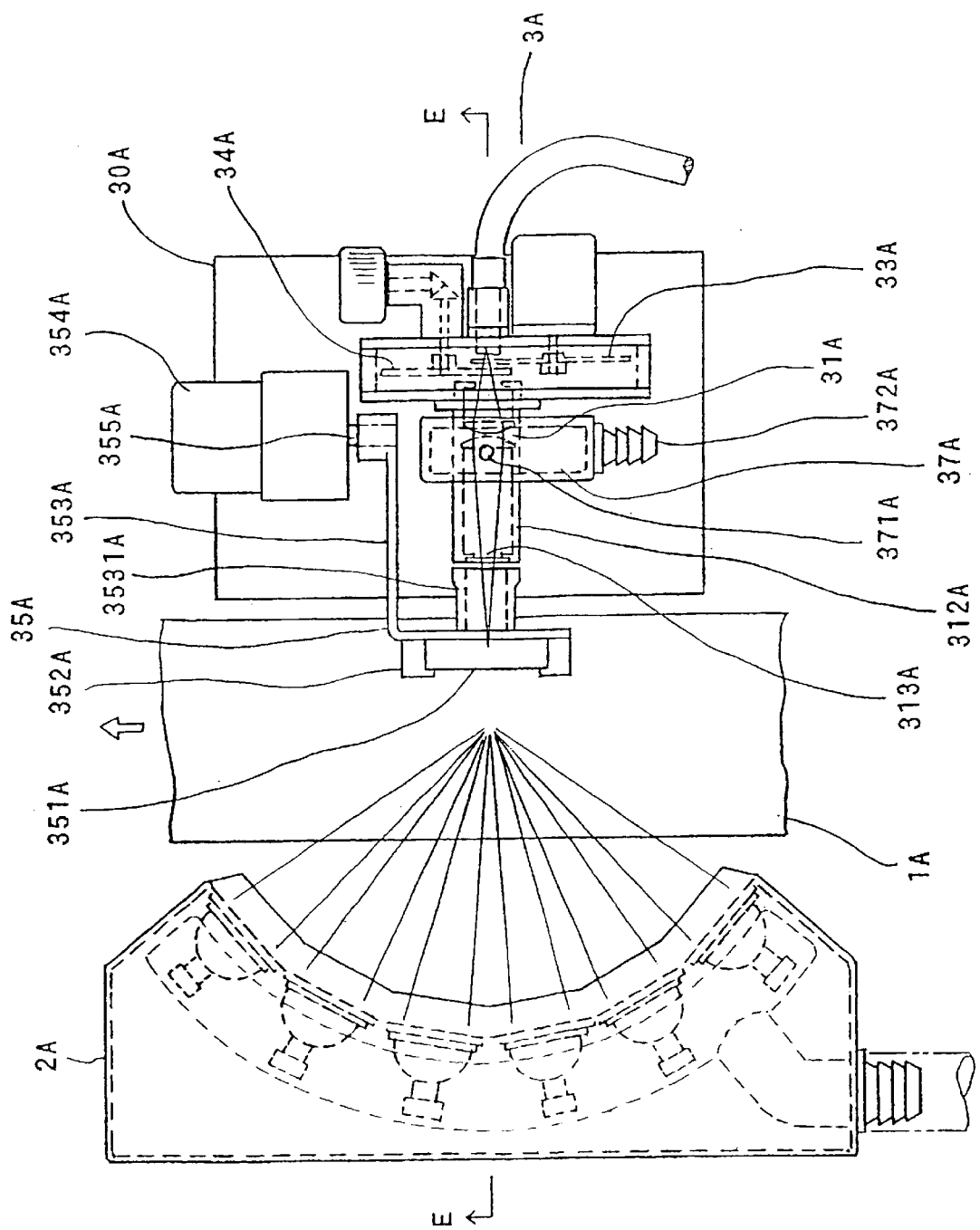
FIG. 9 is a plan view of a second embodiment of the inside-quality inspecting device of this invention, in which the white level calibrator of light receiving means is arranged to operate in the vertical direction of the inspecting device.
Figure 10:
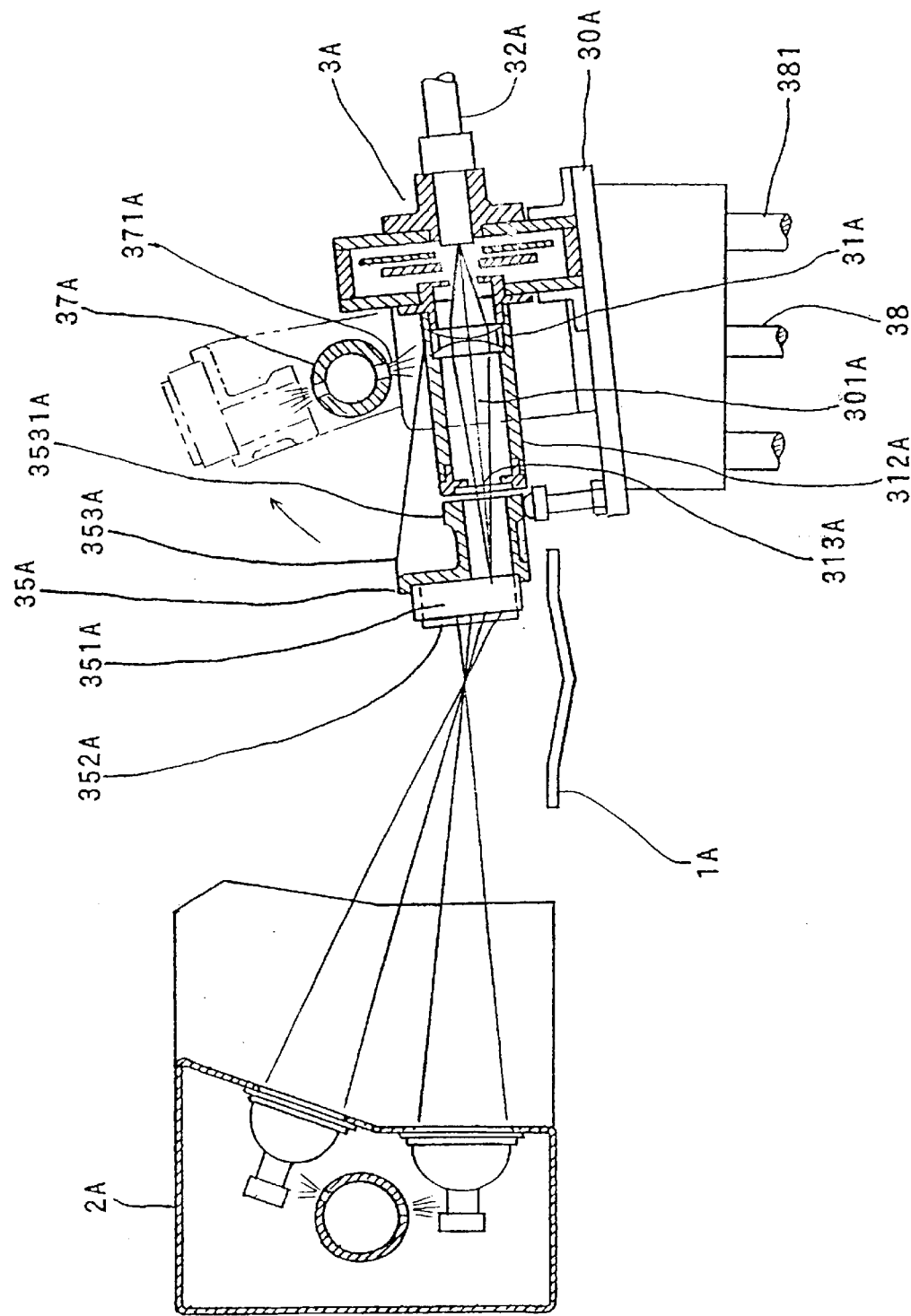
FIG. 10 is a side view of a vertical section taken along a line E—E shown in FIG. 9.

FIGS. 9 and 10 show a second embodiment of the inside-quality inspecting device according to this invention.

In the second embodiment, a white level calibrator 35A of light receiving means 3A differs from the white level calibrator 35 of the first embodiment. In the case of the second embodiment, a mounting arm 353A is arranged to be operated in a different direction in moving a white level calibrating plate 351A forward and backward to and from the front of a condenser lens 31A.

With the exception of the white level calibrator 35A, the condenser lens 31A, an optical fiber 32A, a shutter 33A, a light-reducing-filter mounting plate 34A, etc. of the second embodiment are arranged in the same manner as in the first embodiment. Light-projecting means 2A of the second embodiment is also arranged in the same manner as that of the first embodiment. The details of these parts are, therefore, omitted from the description.

In the case of the second embodiment, the white level calibrating plate 351A is mounted on the mounting arm 353A by means of a retaining metal 352A. The mounting arm 353A is mounted on the rotation shaft 355A of a stepping motor T354A. The white level calibrating plate 351 A is arranged to be moved to a retracted position above the condenser lens 31 A as shown by two-dot chain lines in FIG. 10 and to be moved forward to the front of the condenser lens 31A for a calibrating action. In other words, the white level calibrating plate 351A is moved to the front of the light receiving window 313A of the condenser lens 31A or to a retracted position which is located above the lens hood 312A.

A cylindrical projection 3S31 is formed to extend from the mounting arm 353A toward the lens hood 312 to shield a part between the white level calibrating plate 351A and the light receiving window 313A of the lens hood 312A from surroundings, so that no disturbance light is allowed to come into the light receiving window 313A.

The light receiving means 3A includes a cooling air blowing duct 37A. The cooling air blowing duct 37A is provided with an air blowing nozzle 371A and is arranged to have air from an air blower blown at the tubular projection 353A of the white level calibrating plate 351A. With the cooling air blowing duct 37A arranged in this manner, heat generated by rays of light at the condenser lens 31 A and the white level calibrating plate 351A can be effectively dissipated.

A mount base 30A supports the condenser lens 31A by means of a lifting-and-lowering shaft 38 and a lifting-and-lowering guide 381 which are arranged to vertically adjust the height of the light receiving optical axis 301A of the condenser lens 31A. The lifting-and-lowering shaft 38 is arranged to be driven to vertically move the light receiving means 3A by a motor-driven cylinder, a motor-driven slider or a known linear motion driving mechanism which is not shown but is arranged to use a rack-and-pinion arrangement.

With the embodiment arranged in this manner, the light receiving optical axis is adjusted by moving the mount base 30A to make it lower when the inspecting object is a small fruit item and higher when the inspecting object is a large fruit item.

EMBODIMENT 3

Figure 11:
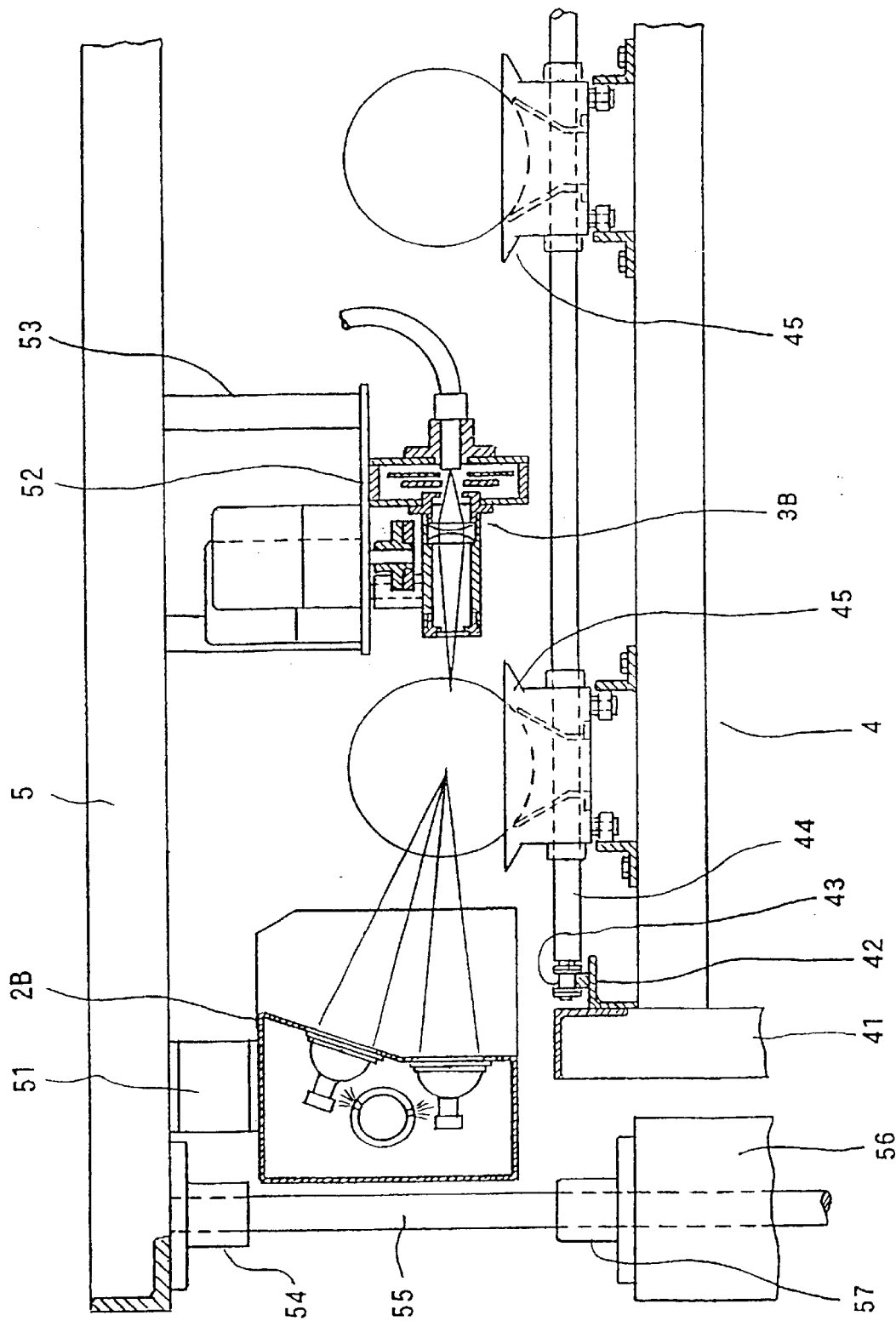
FIG. 11 is a sectional view showing essential parts of a third embodiment of this invention, wherein a chain conveyer consists of a plurality of transport path strips and has receiving trays mounted thereon and the light-projecting means and the light receiving means of the device are arranged to be opposed to each other across each of the transport path strips of the conveyer.

FIG. 11 shows a third embodiment of the inside-quality inspecting device according to this invention. The third embodiment is adapted for a transport conveyer with receiving trays which are arranged to be used in processing inspecting objects in a large quantity.

In FIG. 11, a reference numeral 4 denotes the transport conveyer with receiving trays. Conveyer chains 43 are endlessly stretched on chain rails 42 arranged on the inner sides of a conveyer frame 41. Tray mounting members 44 are arranged in parallel between the conveyer chains 43. Two ends of each tray mounting member 44 are mounted on the conveyer chain 43 on the two inner sides of the conveyer frame 41. A plurality of receiving trays 45 are mounted on each receiving tray mounting member 44 with some spacing intervals provided between them for setting light-projecting means 2B and light receiving means 3B. A plurality of transport paths are thus formed in a shape of spacing strips.

At each strip of the transport paths, the mounting position of the light-projecting means 2B and that of the light receiving means 3B are arranged to deviate forward and rearward with respect to the traveling direction of the transport conveyer 4. The intervals between the spacing strips are arranged to be not excessive.

Each of the light-projecting means 2B and the light receiving means 3B is provided with a mounting part on its upper side and is mounted on the lower side of an upper frame 5. More specifically, the light-projecting means 2B is mounted on the upper frame 5 by means of a lamp box mount metal 51 in such a way as to project beams of light concentratedly on an inspecting object which is on the receiving tray 45. The light receiving means 3B is mounted on the upper frame 5 through a mount base 52 by means of mounting metal 53 in an upside-down posture with respect to the light receiving means of the first embodiment shown in FIGS. 1 and 2.

The structural arrangement of the light-projecting means 2B and the light receiving means 3B of the third embodiment is the same as that of the first and second embodiments described. Therefore, the details of them are omitted from the following description.

The upper frame 5 has a lifting-and-lowering shaft 55 extending downward from a bracket 54. A lower frame 56 has a bearing 57 arranged to have the shaft 55 to extend therethrough. A lifting-and-lowering unit which is not shown is arranged within the lower frame 56 to move the upper frame 5 upward or downward, through the shaft 55, to adjust the position of the light-projecting means 2B which concentratedly projects light and that of the light receiving means 3B to the size of the object on the receiving tray 45.

The lifting-and-lowering unit which is not shown is arranged to move the light-projecting and -receiving means 2B and 3B upward or downward by a known linear motion driving mechanism such as a motor-driven cylinder, a motor-driven slider or a rack-and-pinion mechanism.

According to the arrangement of the third embodiment described above, a large amount of inspecting objects can be processed to inspect the internal quality of them by using one transport conveyer which is arranged to convey them on receiving trays aligned in a plurality of strips.

INDUSTRIAL APPLICABILITY

According to this invention, as described in the foregoing, beams of light are concentratedly projected on the inspecting objects obliquely from one side of them by a plurality of light-projecting lamps while they are conveyed on a conveyer in such a way as to cover a wide surface area of each of them ranging from an obliquely front area to an obliquely rear area. Therefore, even in the event of inspecting an agricultural product having a thick skin, the projected light can penetrate through various inner parts of the inspecting object. Even in cases where the inside-quality of the object on its sunny side differs from its shadow side in respect of a sugar forming degree, acidity or the like, information oil the inside-quality covering a wide range is obtained from transmitted light coming to the opposite side of the object, so that averaged inside-quality data can be obtained for each inspecting object.

According to this invention, a plurality of light-projecting, lamps are arranged to project beams of light in a concentrating manner. Since this arrangement permits use of small lamps individually having a relatively small output, they do not generate much heat, so that the service life of the lamps can be lengthened while the other parts around them can be saved from being affected by any excessive heat.

Further, according to this invention, the shutter is provided between the condenser lens and the light input face of the optical fiber which leads the condensed transmitted light to the spectroscope. The shutter enables the inspecting device to do spectral analysis by allowing the spectroscope to receive only the light transmitted through the center portion of the object while the object is traveling on the transport conveyer.

In one aspect of the invention, the inspecting device provides that the condenser lens is encompassed with the dust-proof lens hood, which defines a visual field on the objective side of the lens. Therefore, while the transmitted light coming from the front of the condenser lens is allowed to be incident on the optical fiber, all disturbance light that exists outside of the visual field is not allowed to be incident on the optical fiber. The lens hood thus enables the inspecting device to carry out spectral analysis without being affected by any disturbance light. The means for moving the white level calibrating plate is arranged to move the white level calibrating plate to and from the front of the condenser lens under the above-stated condition. By virtue of that arrangement, the white level calibration can be promptly made not only before a start of the inspecting device but also when changes take place in temperature or in environmental conditions and also when the inspecting operation is in pause. Therefore, the spectral analysis can be always reliably carried out.

According to the arrangement in another embodiment of this invention, the adverse effects of unnecessary scattering light coming into the lens hood and stray light such as flares taking place inside of the lens hood are eliminated to allow only the light transmitted through the inspecting object is led to the light inputting face of the optical fiber. Therefore, the arrangement enhances the accuracy and reliability of the results of the spectral analysis.

According to the arrangement in yet another embodiment, the cooling air is blown at the condenser lens and the white level calibrating plate which receives the light of the light-projecting means. Therefore, the results of spectral analysis is effectively prevented from being affected by a gradual temperature increase of the light receiving means.

According to the arrangement in a further embodiment, the reflecting power of the small sealed lamps having the focal point of their beams at the inspecting object never decreases. Since the small lamps are thus arranged to be easily handled, the beams of light can be projected by using many of them from a wide range of different directions.

The sealed lamps never overheat as the cooling air is blown at their sealed parts. These sealed lamps are thus arranged to have halogen gas circulate inside of them in a state of being not excessively heated nor excessively cooled, so that their service lives can be increased by the arrangement.

Further, since the arrangement according to this invention permits the operator of the inspecting device to vary the quantity of projecting light by increasing or decreasing the number of light-projecting lamps to be used for inspection, the inside-quality inspection can be made for inspecting objects of a wide range of different kinds including agricultural products having thick skins such as watermelons, melons and thick-skin tangerines and having thin skins such as apples, peaches, pears, etc.

Since the height of the light-projecting lamps is adjustable according to the size of the inspecting objects, such as melons, apples, tangerines, etc. by remote control, the arrangement to use the inspecting device for one kind of object can be promptly and easily switched over to the arrangement to use it for another kind of object.

According to another aspect of the invention, the quantity of light incident on the spectroscope is adjustable by selectively inserting light reducing filters of varied kinds into the transmitted-light-receiving optical path of the light receiving means even when the quantity of transmitted light varies with the kind or item of the inspecting object. In cases where the amplifying degree of the operational amplifier of the spectral analyzer has been adjusted beforehand to an item having a small quantity of transmitted light, the spectral analysis can be stably carried out without overflowing by selecting and using one of the light reducing filters if the current inspecting object is of a kind giving a larger quantity of transmitted light.

According to yet another aspect of this invention, no light is allowed to come through the optical fiber, so that the light receiving element of the spectroscope can be kept at its zero level, except when the transmitted light obtained from the central inspecting part of the object is to be examined. The output of the spectroscope, therefore, always builds up from zero to give a reliable result of analysis every time the inspection is made on one object.

According to a further aspect of this invention, the electronic shutter which is included in the control circuit of the light receiving element disposed in rear of the spectroscope can be continuously operated at a high speed because the shutter includes no mechanical element. Therefore, the processing capability per unit time of the inspecting device can be enhanced by increasing the speed of the transport conveyer.

It has been a shortcoming of conventional spectral analyzers that their calibration curves come to deviate from a normal state and fluctuate with the changes of temperature and the lapse of operating time in cases where they are in operation for several hours every day. According to a still further aspect of this invention, on the other hand, the spectral analyzer always uses a calibration curve in an optimum state irrespective of changes in temperature and the length of operation time, because the embodiment of this invention is arranged to make calibration with a white level calibrating plate and also to correct deviations by making spectral analysis on light transmitted through the vessels containing therein reference materials such as sugar and acid materials.

The inside-quality inspecting device arranged to have the above-stated advantages according to this invention is best suited for use in combination with a screening-and-sorting conveyer for sorting agricultural products and the like by quality.

While the foregoing description and drawings represent the present invention, it will be obvious to those skilled in the art that various changes may be made therein without departing from the true spirit and scope of the present invention.

Description of reference numeral

| | |
|---|---|
| 1, 1A | transport conveyer |
| 11 | inspecting position |
| 2, 2A, 2B | light projecting means |
| 21 | light projecting lamp |
| 211 | beam angle |
| 212 | paraboloidal reflecting mirror |
| 213 | sealing glass |
| 214 | seal part |
| 215 | socket |
| 22 | lamp box |
| 23 | lamp side cooling air blowing duct |
| 231 | nozzle |
| 232 | connection port |
| 3, 3A, 3B | light receiving means |
| 30, 30A | mount base |
| 301, 301A | light receiving optical axis |
| 31, 31A | condenser lens |
| 311 | focal point on objective side |
| 312, 312A | lens hood |
| 313, 313A | light receiving window |
| 314 | orifice plate |
| 32, 32A | optical fiber |
| 321 | light inputting face |
| 33, 33A | shutter |
| 331 | cutaway parts |
| 332 | stepping drive unit |
| 34, 34A | light-reducing-filter mounting plate |
| 341 | filter mounting holes |
| 342 | light reducing filters |
| 343 | shaft |
| 344 | knob handle |
| 345 | miter gear |
| 35, 35A | white level calibrator |
| 351, 351A | white level calibrating plate |
| 3511 | peripheral face of calibrating plate |
| 352, 352A | retaining metal |
| 353, 353A | mounting arm |
| 3531, 3531A | tubular projection |
| 354 | stepping motor R |
| 354A | stepping motor S |
| 355, 355A | rotation shaft |
| 356, 358 | detection switches |
| 357, 359 | detection pieces |
| 36 | reference material check unit |
| 361 | quality reference material |
| 3611 | peripheral face of material |
| 362 | vessel |
| 3621 | plug |
| 363 | mounting arm |
| 3631 | light blocking wall part |
| 3632 | vessel loading part |
| 3633 | upper retainer |
| 3634 | peep hole |
| 364 | stepping motor T |
| 3641 | output shaft |
| 37, 37A | cooling air blowing duct for light receiving means |
| 371, 371A | nozzles |
| 372, 372A | connection ports |
| 38 | lifting-and-lowering shaft |
| 381 | lifting-and-lowering guide |
| 4 | transport conveyer with receiving trays |
| 41 | conveyer frame |
| 42 | chain rail |
| 43 | conveyer chain |
| 44 | receiving tray mount |
| 45 | receiving tray |
| 5 | upper frame |
| 51 | lamp box mount metal |
| 52 | mount base |
| 53 | mount metal |
| 54 | bracket |
| 55 | lifting-and-lowering shaft |
| 56 | lower frame |
| 57 | bearing |
| F | agricultural product |

What is claimed is:

1. A side multi-lamp type on-line inside-quality inspecting device comprising:

a transport conveyer arranged to convey inspecting objects one by one;

light projecting means arranged to use a plurality of light projecting lamps and to project beams of light toward the center part of the inspecting object being conveyed in a concentrative manner from different positions on one side of the transport path of said transport conveyer and at different angles covering a surface area of the object ranging from an obliquely front part to an obliquely rear part on one side of the object when the inspecting object comes to pass an inspecting position on the transport path;

light receiving means for receiving light transmitted through the inside of the inspecting object with the beams of light projected thereon, said light projecting means and said light receiving means being opposed to each other across the transport path of said transport conveyer; and means for inspecting the inside-quality of the inspecting object by converging and by making spectral analysis on the light transmitted through the inside of the inspecting object;

said light receiving means including:

a lens hood which has a light receiving window formed by using transparent glass in a front part and on the object side of the light receiving means in such a way as to receive light transmitted from a measuring part of the inspecting object and to define and limit the visual field of a light receiving lens;

a diaphragm or an orifice plate arranged within said lens hood to prevent scattering light coming from parts other than the measuring part of the object; and a light passage opening-and-closing mechanism having a shutter arranged to open and close a passage of the transmitted light within a dark box which tightly seals surroundings including the passage of light leading to the light entrance or inputting face of an optical fiber which is connected to said lens hood to lead light from said light receiving window to a spectroscope, said light passage opening-and-closing mechanism being arranged to cause said shutter to open every time the center part of one inspecting object passes in front of said lens hood and to be closed when non-inspecting parts, such as the front and rear end parts, of the object are passing and when no inspecting operation is performed.

2. The side multi-lamp type on-line inside-quality inspecting device according to claim 1, wherein white-level calibration-plate moving means is arranged to move a white level calibration plate forward and backward to and from a position where a peripheral surface part on the lens side of the inspecting object passes between said light projecting means and said light receiving window of said lens hood of said light receiving means in a non-contact manner and without being sealed and in such a way as to permit calibration.

3. The side multi-lamp type on-line inside-quality inspecting device according to claim 2, further comprising air cooling means which includes air nozzles and a cooling air blowing duct for said lens hood of said light receiving means and for said white level calibrating plate in a stand-by position outside of the transport path and is arranged to dissipate radiant heat caused by the rays of light projected on the lens hood and said white level calibrating plate by supplying air from an air blower to said cooling air blowing duct.

4. The side multi-lamp type on-line inside-quality inspecting device according to claim 2, further comprising a quality reference material check device arranged to selectively move inch by inch a plurality of quality reference materials, in front of the light receiving window of said lens hood of said light receiving means, forward to and backward from a position where a peripheral surface part on the lens side of the inspecting object and parts around said part come to pass, and wherein said check device is used as means for correcting any fluctuations due to aging of a spectral analyzer on the basis of fluctuations taking place in the light transmitted through said quality reference material.

5. The side multi-lamp type on-line inside-quality inspecting device according to claim 1, wherein:

each of said plurality of light projecting lamps of said light projecting means which is opposed to said light receiving means across said transport path is a sealed lamp having a reflecting mirror of a parabolic surface to form a beam angle at which a focal point is obtained where the inspecting position becomes the center part of the inspecting object;

said plurality of light projecting lamps are arranged to have their light projecting optical axes deviate from each other at such angles and positions that the beams of light passing through the focal point do not rectilinearly come into the light receiving optical axis of said light receiving means;

a cooling air blowing duct is arranged along the sealed part and the socket of each of said light projecting lamps;

said cooling air blowing duct is provided with an air nozzle which is arranged to blow air directly at the sealed part at which each of said lamps tends to have a high heat and a high temperature; and heat dissipating means is arranged to prevent overheating of each of said light projecting lamps by dissipating heat generated at each lamp body with said cooling air blowing duct and said air nozzle by sending air from an air blower to said cooling air blowing duct.

6. The side multi-lamp type on-line inside-quality inspecting device according to claim 1, further comprising:

lifting-and-lowering means for causing by remote control the installed height of a lamp box in which said plurality of light projecting lamps of said light projecting means is mounted to be vertically shifted, for switch-over of on-line inspecting objects from one over to another kind among the inspecting objects having different sizes in the direction of height with reference to the transport plane of said transport conveyer, in such a manner that only the installed height of the light projecting optical axes can be adjusted to the limits of not having the light projecting axes rectilinearly come to the optical axis of said light receiving means; and another lifting-and-lowering means for causing the installed height of the mount base of said light receiving means by remote control to be vertically shifted in such a manner that only the height of the light receiving optical axis can be adjusted to the limits of not having the light projecting optical axes of the light projecting means rectilinearly come to the light receiving axis, said device thus being characterized in that the height of said light projecting means and that of said light receiving means are respectively adjustable.

7. The side multi-lamp type on-line inside-quality inspecting device according to claim 1, wherein:

said light receiving means is provided with a filter mounting plate which orthogonally intersects the transmitted light passage from the light receiving window of said lens hood to the light entrance face of said optical fiber and has a plurality of filter mounting holes;

one of said plurality of filter mounting holes is arranged to be a blank hole while light reducing filters of different light reducing rates are mounted respectively on other filter mounting holes;

the use of said light reducing filters is arranged to be changeable from one filter over to another by selectively adjusting the centers of said holes to the center position of said light receiving optical axis by means of a shaft on which said filter mounting plate is mounted;

filter change-over means is arranged to permit changeover of the use of said light reducing filters from one to another by rotating said shaft according to the item and kind of the inspecting object; and the light transmitted from the inspecting object to said optical fiber is allowed to pass through said blank hole if the quantity of light transmissible by the inspecting object is small and to pass through one of said light reducing filters selected to reduce the quantity of light incident on said optical fiber in case where the transmissible quantity of light by the inspecting object is large, so that spectral analysis can be made by adequately adjusting the quantity of light incident on said spectroscope.

* * * * *